US00PP11560P

United States Patent [19]

Van Hee

[11] Patent Number: Plant 11,560

[45] Date of Patent: Oct. 10, 2000

[54] DAHLIA PLANT NAMED 'DAPAROS'

[75] Inventor: François Van Hee, Enkhuizen, Netherlands

[73] Assignee: Ball Floraplant, a division of Ball Horticultural Company, West Chicago, Ill.

[21] Appl. No.: 09/221,688

[22] Filed: Dec. 28, 1998

[51] Int. Cl.[7] ..... A01H 5/00

[52] U.S. Cl. ..... Plt./321

[58] Field of Search ..... Plt./321

*Primary Examiner*—Howard J. Locker
*Assistant Examiner*—Kent L. Bell
*Attorney, Agent, or Firm*—C. A. Whealy

[57] ABSTRACT

A distinct cultivar of Dahlia plant named 'Daparos', characterized by its fully double red purple inflorescences; uniform growth habit; dark green foliage; and strong peduncles that hold inflorescences above the foliage.

1 Drawing Sheet

BACKGROUND OF THE INVENTION

The present invention relates to a new and distinct variety of Dahlia plant, botanically known as *Dahlia variabilis*, and hereinafter referred to by the name Daparos.

The new Dahlia is a naturally-occurring mutation of the yellow-flowered *Dahlia variabilis* 'Margaret' disclosed in U.S. Plant Pat. No. 6,769. The new Dahlia was discovered by the Inventor in a controlled environment in Enkhuizen, The Netherlands, within a population of plants of 'Margaret'. The selection of this plant was based on its fully double red purple inflorescences.

Asexual reproduction of the new Dahlia by terminal cuttings harvested in Enkhuizen, The Netherlands, has shown that the unique features of this new Dahlia are stable and reproduced true to type in successive generations.

BRIEF SUMMARY OF THE INVENTION

The new Dahlia has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Daparos'. These characteristics in combination distinguish 'Daparos' as a new and distinct cultivar:

1. Fully double red purple inflorescences.

2. Dark green foliage.

3. Strong peduncles that hold inflorescences above the foliage.

The new Dahlia differs from the sibling cultivar 'Dapavio', disclosed in U.S. Plant patent application Ser. No. 09/221,689, most prominently in ray floret color. Additionally, plants of the new Dahlia are less compact than plants of 'Dapavio'.

The new Dahlia is somewhat similar in ray floret color to the Dahlia cultivar 'Lizzy', disclosed in U.S. Plant Pat. No. 9,846. However in side-by-side comparisons conducted in West Chicago, Ill., plants of the new Dahlia differ from plants of the cultivar 'Lizzy' in the following characteristics:

1. Plants of the new Dahlia are taller and broader than plants of the cultivar 'Lizzy'.

2. Plants of the new Dahlia have smaller, darker green, and more numerous leaves than plants of the cultivar 'Lizzy'.

3. Plants of the new Dahlia have smaller inflorescences, but are more floriferous than plants of the cultivar 'Lizzy'.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical plant of the new Dahlia. Ray floret and foliage colors may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown outdoors in West Chicago, Ill., in 11.5-cm containers in a glass greenhouse with average day and night temperatures of 22 and 18° C., respectively.

Botanical classification: *Dahlia variabilis* 'Daparos'.

Parentage: Naturally-occurring mutation of *Dahlia variabilis* 'Margaret', disclosed in U.S. Plant Pat. No. 6,769.

Propagation:

*Type.*—By terminal cuttings.

*Time to initiate roots.*—About 7 days with temperatures of 18° C.

*Time to develop roots.*—About 21 days with temperatures of 18° C.

*Rooting habit.*—Terminal cuttings propagate easily, roots fibrous and well-branched.

*Tubers.*—Plants of the new Dahlia will form tubers under short day conditions, that is at least 13 to 14 hours of darkness. Tubers are roughly thumb-shaped, about 1.9 cm in width and about 3.2 cm in length.

Plant description:

*Appearance.*—Pot plant and perennial garden plant. Upright and uniform growth habit, rounded apex. Moderate growth rate and moderately vigorous. Appropriate for 10 to 12.5-cm containers. Plants typically flower about 8 weeks after planting rooted cuttings.

*Plant height.*—About 27 cm.

*Plant spread.*—About 24 cm.

*Stem description.*—Quantity: About five per plant. Basally branching, however, plants typically require pinching to enhance lateral branch development. Lateral branch length: About 19 cm. Lateral branch diameter: About 5 mm. Internode length: About 2 cm. Texture: Smooth. Color: 144C.

*Foliage description.*—Arrangement: Young foliage, leaves single; fully expanded foliage, leaves compound, trifoliate; opposite. Quantity of leaves per lateral branch: About 12. Leaf length: About 6.5 cm. Leaf width: About 5.5 cm. Terminal leaflet length: About 5.5 cm. Terminal leaflet width: About 3.5 cm. Leaflet shape: Ovate. Leaflet apex: Acuminate. Leaflet base: Attenuate. Leaflet margin: Serrate to dentate. Texture: Slightly velvety, pubescence on both surfaces. Petiole length: About 2.3 cm. Petiole diameter: About 2 mm. Color: Fully expanded foliage, upper surface: 147A with 144C venation. Fully expanded foliage, lower surface: 147B with 144C venation. Petiole: 144C.

Flowering description:

*Appearance.*—Fully double inflorescence form. Inflorescences generally hemispherical and borne on terminals above foliage, arising from leaf axils on strong peduncles; inflorescences face upright. Typically about four inflorescences and buds per lateral stem. Disc and ray florets arranged acropetally on a capitulum. Persistent. Inflorescences typically last about nine days on the plant. Inflorescences are not fragrant.

*Flowering response.*—Under natural conditions, plants flower intermittently from July to October in the Northern Hemisphere.

*Flower bud (just before opening).*—Shape: Rounded to flat. Length: About 1.9 cm. Diameter: About 1.6 cm.

*Inflorescence size.*—Diameter: About 8 cm. Depth (height): About 4 cm. Disc diameter: About 8 mm.

*Ray florets.*—Quantity per inflorescence: About 60. Shape: Elliptic, cupped. Length: About 2.5 cm. Width: About 2 cm. Apex: Rounded to slightly pointed. Base: Attenuate. Margin: Entire. Texture: Satiny, glabrous. Color: When opening, upper surface: 71A. When opening, lower surface: 71B. Fully opened, upper surface: Center, 59B; margins, lighter than 72A. Fully opened, lower surface: 72B.

*Disc florets.*—Elongated, cylindrical; few, typically less than 10.

*Peduncle.*—Aspect: Erect and strong. Length: About 6 cm. Texture: Smooth. Color: 144C.

*Involucral bracts.*—Quantity: About 6. Shape: Sharply elliptic. Tip: Acute. Margin: Entire. Texture: Smooth, shiny. Color: Upper, 147A; lower, 147B.

*Reproductive organs.*—Androecium (Present on disc florets): Pollen amount: Moderate. Pollen color: 23A. Gynoecium present on ray and disc florets.

Disease resistance: Resistance to known Dahlia diseases has not been observed on plants grown under commercial greenhouse conditions.

Seed production: Seed production has not been observed.

It is claimed:

1. A new and distinct cultivar of Dahlia plant named 'Daparos', as illustrated and described.

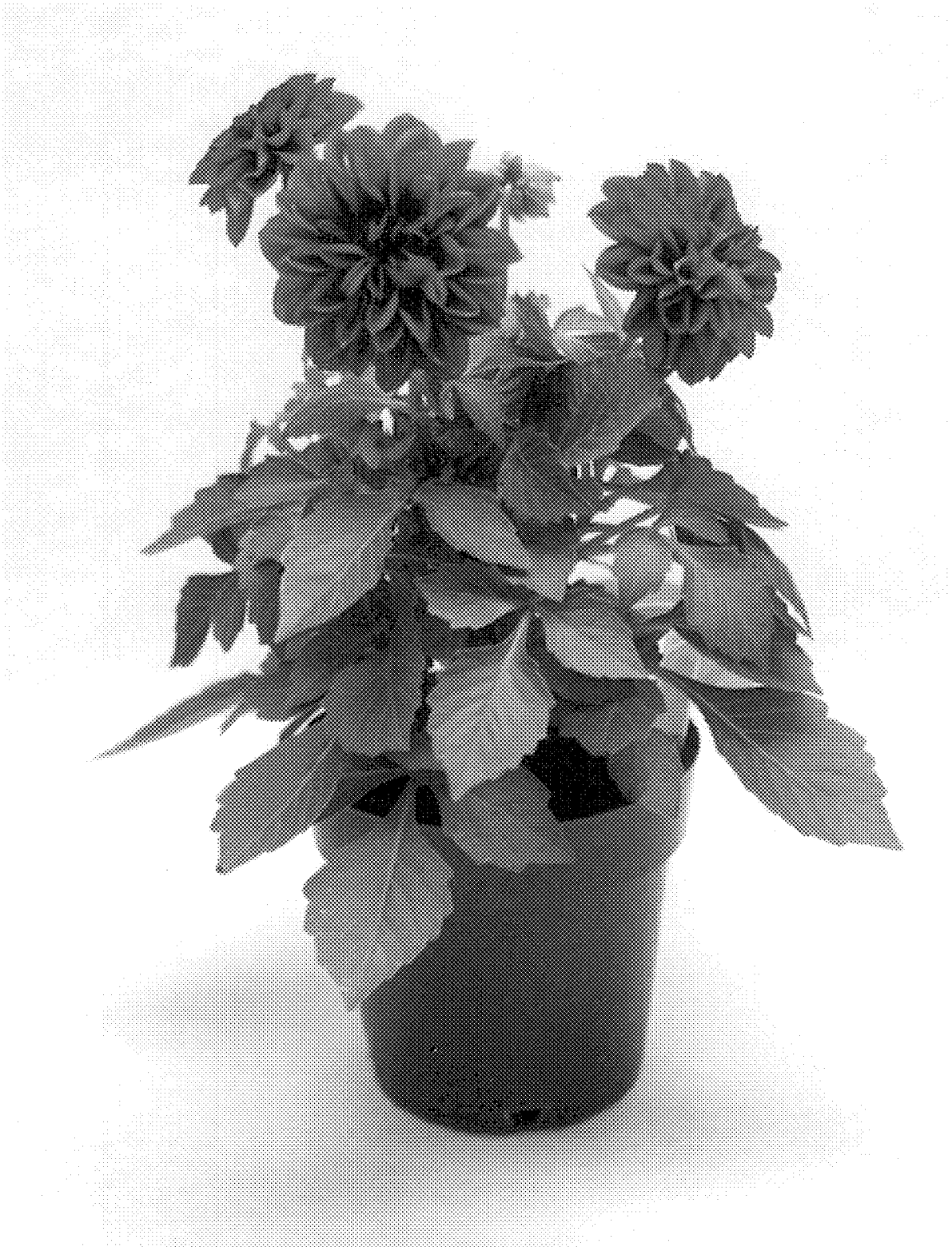

* * * * *